United States Patent [19]

Blythin et al.

[11] Patent Number: 4,782,067

[45] Date of Patent: Nov. 1, 1988

[54] ANTI-ALLERGIC COMPOSITION CONTAINING ZWITTERIONIC BICYCLIC COMPOUNDS

[75] Inventors: David J. Blythin, North Caldwell; Ho-Jane Shue, Pine Brook, both of N.J.

[73] Assignee: Schering Corporation, Kenilworth, N.J.

[21] Appl. No.: 76,469

[22] Filed: Jul. 22, 1987

Related U.S. Application Data

[63] Continuation-in-part of Ser. No. 760,196, Jul. 29, 1985, Pat. No. 4,684,727.

[51] Int. Cl.$^4$ .......................................... A61K 31/435
[52] U.S. Cl. .................... 514/300; 514/212; 514/239; 514/242; 514/222; 514/249; 514/253; 514/254; 514/256; 514/304; 514/305; 514/312; 514/216
[58] Field of Search ............... 514/216, 239, 242, 253, 514/249, 256, 300, 304, 305, 312, 254, 212

[56] References Cited

U.S. PATENT DOCUMENTS 4,264,602 4/1981 Hardtmann ..................... 424/256

FOREIGN PATENT DOCUMENTS 0092786 11/1983 European Pat. Off. .

OTHER PUBLICATIONS

Kappe et al., Monatshefte fur Chemie, 99, pp. 2157–2166 (1968).
Merchant et al., Curr. Sci., 49(1), pp. 20–21, (1980); Chem. Abst. vol. 92-181059u (1980).
Wittman et al., Z. Naturforsch., B: Anorg. Chem., Org. Chem., 33B(12), pp. 1540-1546 (1978); Chem. Abst. vol. 90-121339 (1979).
Bowman et al., "The Synthesis of Some Dialkylamino-2-Quinolones," Journal of the Chemical Society, pp. 1350–1353 (1964).
Suzuki et al., Chemical Pharmaceutical Bulletin, 25 (No. 10) 2602–2607 (1977).

Primary Examiner—Mary C. Lee
Assistant Examiner—Bernard I. Dentz
Attorney, Agent, or Firm—James R. Nelson; Richard C. Billups; Stephen I. Miller

[57] ABSTRACT

Zwitterionic bicyclic compounds are disclosed which are useful as anti-allergic, anti-inflammatory and/or cytoprotective agents and in the treatment of hyperproliferative skin disease. Pharmaceutical compositions and methods of treatment employing such compounds are also disclosed.

40 Claims, No Drawings

ANTI-ALLERGIC COMPOSITION CONTAINING ZWITTERIONIC BICYCLIC COMPOUNDS

The present application is a continuation-in-part of copending U.S. application Ser. No. 760,196 filed July 29, 1985 now U.S. Pat. No. 4,684,727.

BACKGROUND OF THE INVENTION

The present invention relates to certain zwitterionic bicyclic compounds and to pharmaceutical compositions and methods of use employing such compounds.

An article by Bowman et al. entitled "The Synthesis of Some Dialkylamino-2-quinolones," *Journal of the Chemical Society*, pp. 1350–1353 (1964), discloses certain 1-alkyl-3-dialkylamino-4-hydroxy-2-quinolones. Mentioned in this article are 3-dimethylamino-4-hydroxy-1-phenyl-2-quinolone and 1-benzyl-3 dimethylamino-4hydroxy-2-quinolone. No utility is mentioned in the article for such compounds.

Certain other 3-amino substituted quinolones are disclosed in Kappe et al., *Monatshefte fur Chemie*, 99, pp. 2157–2166 (1968); Merchant et al., *Curr. Sci.*, 49(1), pp. 20–21 (1980); and Wittmann et al. *Z. Naturforsch., B: Anorg. Chem., Org. Chem.*, 33B(12), pp. 1540–1546 (1978).

SUMMARY OF THE INVENTION

The invention in its pharmaceutical composition aspect comprises a compound having the structural formula I or a pharmaceutical acceptable salt or solvate thereof, in a combination with a pharmaceutically acceptable carrier, wherein:

W and X may be the same or different and each independently represents —CH= or —N=;

$Z_1$ and $Z_2$ are the same or different and each independently represents O or S;

$R^1$, $R^2$, $R^3$, $R^4$ and $R^5$ are the same or different and each may be independently selected from the group consisting of H, alkyl having from 1 to 12 carbon atoms, alkenyl having from 3 to 8 carbon atoms, alkynyl having from 3 to 8 carbon atoms, alkoxyalkyl having from 1 to 6 carbon atoms in the alkoxy portion and from 2 to 6 atoms in the alkyl portion thereof, hydroxyalkyl having from 2 to 8 carbon atoms, cycloalkyl having from 3 to 8 carbon atoms, acyloxyalkyl having from 1 to 6 carbon atoms in the acyloxy portion and from 2 to 8 carbon atoms in the alkyl portion thereof, and —R$^6$—CO$_2$R$^0$ wherein R$^6$ represents an alkylene group having from 1 to 6 carbon atoms and R$^0$ represents hydrogen or an alkyl group having from 1 to 6 carbon atoms, with the provisos that the OH of the hydroxyalkyl group and the acyloxy of the acyloxyalkyl group are not joined to the same carbon atom as another heteroatom and that, when $R^1$, $R^2$ and/or $R^3$ are alkenyl or alkynyl, there is at least one carbon-carbon single bond between the nitrogen atom and the carbon-carbon double or triple bond;

in addition, one of $R^1$, $R^2$ or $R^3$ can be an aryl group or a heterocyclic group, either of which can be substituted with one to three substituents Y as defined below;

in further addition, two of $R^1$, $R^2$ and $R^3$ can be joined together to represent a ring which can contain from 2 to 8 carbon atoms, said ring optionally containing a —O—, —S— and/or —NR$^4$— heteroatomic group (wherein R$^4$ is as defined above) and/or optionally containing a carbon-carbon double bond, and said ring optionally being substituted with one to three additional substituents R$^7$ which substituents may be the same or different and are each independently selected from OH with the proviso that OH is not on a carbon already joined to a hetero atom, —O—acyl having from 1 to 6 carbon atoms, hydroxyalkyl having from 1 to 8 carbon atoms, alkoxyalkyl having from 1 to 6 carbon atoms in each alkyl portion thereof, alkyl having from 1 to 6 carbon atoms, alkenyl having from 3 to 8 carbon atoms, alkynyl having from 3 to 8 carbon atoms, —COOR$^{10}$ wherein R$^{10}$ is H alkyl or aryl, or any two R$^7$ substituent groups may represent a hydrocarbon ring having from 4 to 8 total carbon atoms; and in still further addition, all three of $R^1$, $R^2$ and $R^3$ can be joined together to represent a polycyclic ring, which polycyclic ring can optionally be substituted by one to three substituent groups R$^7$ as defined above;

m is an integer of from 0 to 3;

n is an integer of from 0 to 2;

Q represents an aryl or an aromatic heterocyclic group which can optionally be substituted with 1 to 3 substituents Y as defined below; and each Y substituent is independently selected from the group consisting of hydroxy, alkyl having from 1 to 6 carbon atoms, halogen, NO$_2$, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, hydroxyalkyl having from 1 to 6 carbon atoms, —S(O)$_n$—R$^8$ (wherein R$^8$ represents alkyl having from 1 to 6 carbon atoms and n is as defined above), —SO$_2$NH$_2$, —CO—R$^9$ (wherein R$^9$ represents OH, —NH—R$^8$ or —O—R$^8$, where R$^8$ is as defined above), —O—B—COR$^9$ (wherein B represents an alkylene group having from 1 to 4 carbon atoms and R$^9$ is as defined above), —NH$_2$, —NHCHO, —NH—CO—R$^9$ (wherein R$^9$ is as defined above, with the proviso that it is not hydroxy), —NH—COCF$_3$, —NH—SO$_2$R$^8$ (wherein R$^8$ is as defined above), and —NHSO$_2$CF$_3$.

A preferred subgenus of compounds is represented by those compounds in which at least one of W and X is N. More preferably, W is CH and X is N. Moreover, at least one of $Z_1$ and $Z_2$ is preferably O and m and n are preferably zero.

An additional preferred subgenus of compounds is represented by the structural formula II wherein $R^1$, $R^2$, $R^3$, Q, $Z_1$ and $Z_2$ are as defined above. Preferably, at least one of $Z_1$ and $Z_2$ is O. In addition, Q is preferably an aryl group, which may be optionally substituted with one to three Y groups, more preferably, one or two Y groups.

The compounds of the invention, because of their zwitterionic character, provide good solubility in physiological fluids, such as blood, plasma, saliva, etc., and in general in polar solvents, such as water and ethanol, which can be used in compositions for delivering the compounds to patients. This characteristic is advantageous in that the compounds are expected to be more easily absorbed gastrointestinally and therefore provide good activity when administered orally.

The invention in a first pharmaceutical method aspect is a method for treating allergic reactions in a mammal which comprises administering an anti-allergic effective amount of the above-defined pharmaceutical composition to the mammal.

The invention in a second pharmaceutical method aspect is a method for treating inflammation in a mammal which comprises administering an anti-inflammatory effective amount of the above-defined pharmaceutical composition to the mammal.

The invention in a third pharmaceutical method aspect is a method for treating peptic ulcers in a mammal which comprises administering a cytoprotective effective amount of the above defined pharmaceutical composition to the mammal.

The invention in its chemical compound aspect is a compound having the structural formula I as defined above with the proviso that 3-dimethylamino-4-hydroxy-1-phenyl-2-quinolone and 1-benzyl-3-dimethylamino-4-hydroxy-2-quinolone are excluded. In another aspect the compounds of the invention may have the structural formula I as defined above with the provisos that $-NR^1R^2R^3$ does not represent $-NH(alkyl)_2$ when m=0, n=0, W and X are both $-CH=$, Q=phenyl, $Z_1$=O and $Z_2$=O or when m=1, n=0, W and X are both $-CH=$, $R^4$ and $R^5$ are both H, Q=phenyl, $Z_1$=O and $Z_2$=O.

DETAILED DESCRIPTION OF THE INVENTION

The compounds employed in the present invention may be prepared from a compound of structural formula III:

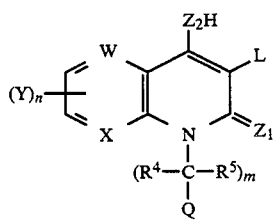

wherein $R^4$, $R^5$, Q, X, Y, W, $Z_1$, $Z_2$, m and n are as defined above and L is a substituent known to those skilled in the art as a "leaving group."

Treatment of a compound of the formula III above with the amine compound of the formula

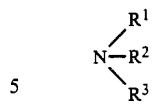

(wherein $R^1$, $R^2$, and $R^3$ are as defined above) with heat in a suitable solvent, such as pyridine, dimethyl formamide, hexamethyl phosphoramide, 2,6-lutidine, dimethyl acetamide and the like, results in formation of the desired product of formula I. The reaction, depending upon the reactants chosen, can be performed at temperatures of about 60° C. up to the reflux temperature of the particular solvent.

For purposes of the invention, a "leaving group" is defined as a substituent which may be displaced and carry a negative charge. Representative examples of suitable leaving groups include chloride, bromide, iodide, trifluoroacetoxy, methanesulfonyloxy, trifluoromethanesulfonyloxy, p-toluene-sulfonyloxy, $-I^+$-Ar, and the like. A preferred leaving group is bromide.

The compound of formula IV above is generally a secondary or tertiary amine, i.e., one in which at most one of the groups $R^1$, $R^2$ or $R^3$ is hydrogen. Such materials are readily obtainable either commercially or by methods well known to one of ordinary skill in the art.

The intermediates of formula III above are either known or can be prepared from corresponding 3-unsubstituted derivatives which are disclosed, for example, in U.S. Pat. No. 4,492,702, the disclosure of which is incorporated herein by reference. For example, a compound of the formula (V)

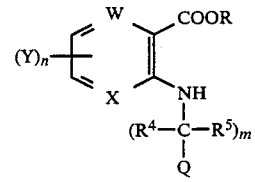

(wherein Q, $R^4$, $R^5$, Y, W, X, n and m are as defined herein and R is any convenient alkyl group) may be reacted with a compound of structural formula VI

(wherein R is again, for example, an alkyl group) to directly produce the compounds of the formula VII

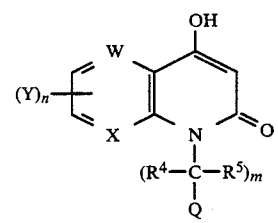

This reaction is preferably accomplished by contacting the two reactants V and VI in the presence of a base such as a metal alkoxide, e.g., potassium tertiary butoxide or the like, at an elevated temperature, e.g., 60° to about 160° C., for a sufficient time until the reaction is substantially completed. The reaction is preferably conducted in an inert atmosphere such as nitrogen. Alternatively, the reaction may be conducted in the presence of a non-reactive solvent such as toluene, xylene, etc.

The compounds of formula VII above can be reacted with a suitable agent to provide the leaving group in the three position on the ring. For example, direct bromination of the compound of formula VII above will provide a compound of III above where L equals Br. As another example, reaction of the compound of VII above with iodosobenzene results in the formation of a compound of formula III where L is -I+-Ph.

The compounds of formula I can also be prepared by reacting a compound of formula V with a compound of formula VIII in the presence of a base:

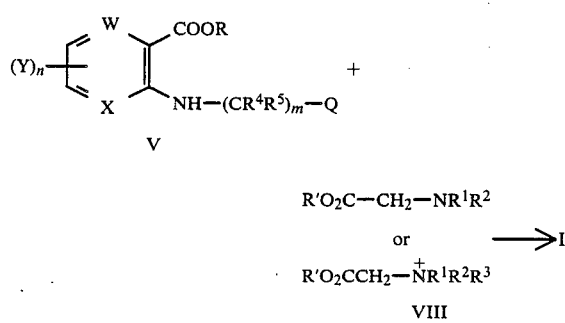

wherein R and R' each independently represents alkyl or aryl. Suitable bases include, for example, NaH, potassium t-butoxide, etc.

Alternatively, a compound of formula V may be reacted with a compund of formula IX or X in the presence of a base (or an epoxide with the compound of formula IX):

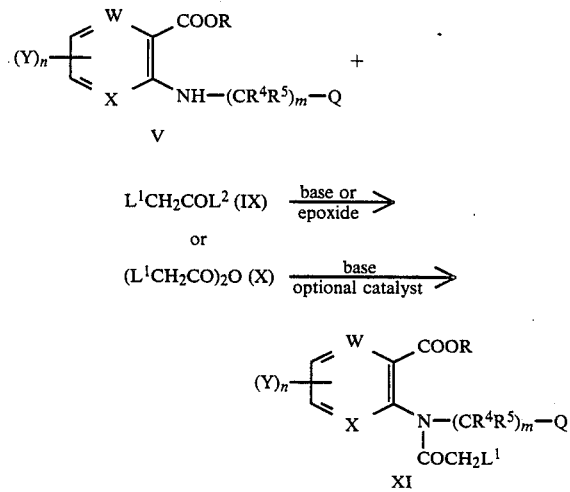

wherein $L^1$ and $L^2$ may be the same or different and each represents a leaving group such as halo and R represents alkyl or aryl. The compound of formula XI is then reacted with a compound of formula IV to form an intermediate of formula XII which may be converted to the final product Ia use of a suitable base such as Li-N(Si(CH$_3$)$_3$)$_2$, sodium methoxide or potassium t-butoxide:

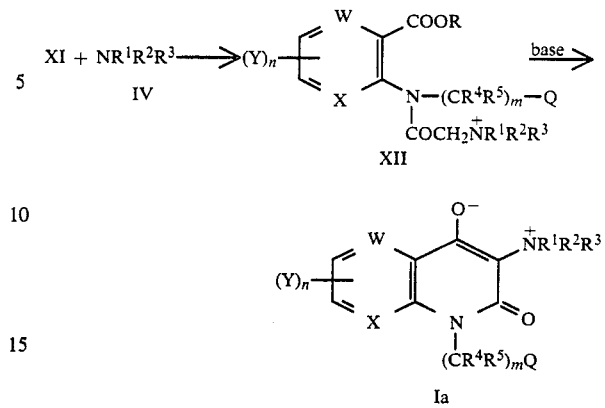

If one of $R^1$, $R^2$ and $R^3$ in formula XII is H, then such H group will be removed when treated with base.

The compounds having structural formula I or Ia above wherein $Z_1$ and $Z_2$ are oxygen may be converted to the corresponding compounds wherein $Z_1$ and/or $Z_2$ are sulfur by known methods. For example, treatment with Lawesson's Reagent [2,4-bis(4-methoxyphenyl)-1,3-dithia-2,4-diphosphetane-2,4-disulfide] in hot toluene will effect this conversion. The isomeric and tautomeric forms can be purified by chromatography of the reaction mixture.

When utilized herein and in the appended claims the below listed terms are defined as follows:

halogen—fluorine, chlorine, bromine and iodine;

alkyl and alkoxy—comprise straight and branched carbon chains and, unless otherwise specified, contain from 1 to 6 carbon atoms;

alkenyloxy—comprise straight and branched carbon chains and, unless otherwise specified, have from 3 to 8 carbon atoms and contain a carbon to carbon double bond;

alkynyloxy—comprise straight and branched carbon chains and, unless otherwise specified, have from 3 to 8 carbon atoms and contain a carbon to carbon triple bond;

aryl—a carbocyclic group containing at least one benzene ring, with the aryl groups preferably containing from 6 to 15 carbon atoms, more preferably being phenyl or Y-substituted phenyl, e.g., phenyl, naphthyl, indenyl, indanyl, 4-chlorophenyl, 4-fluorophenyl, etc.;

aromatic heterocyclic—cyclic groups having at least one O, S and/or N heterogroup interrupting the ring structure and having a sufficient number of unsaturated carbon to carbon bonds, nitrogen to carbon bonds, etc., to provide aromatic character, with the aromatic heterocyclic groups preferably containing from 4 to 14 carbon atoms, e.g., pyridyl, furyl, thienyl, thiazolyl, imidazolyl, pyrimidinyl, pyrazinyl, pyridazinyl, 1,2,4-triazinyl, benzofuranyl, indolyl, pyrazolyl, oxazolyl, etc. Many times such heterocyclic groups can be bonded via various positions on the ring and all such variations are contemplated, e.g. 2- or 3-furanyl, 2-, 3- or 4-pyridyl, etc.

The compounds of the invention contain a $-(CR^4R^5)_m-$ substituent wherein each $R^4$ group and each $R^5$ group may vary independently. Thus, for example, when m equals 2 the following patterns of substitution (wherein hydrogen and CH$_3$ are used to represent any substituent, $R^4$ or $R^5$,) are contemplated:
—C(CH$_3$)$_2$CH$_2$—, —CH$_2$C(CH$_3$)$_2$—, —CH$_2$CH- (CH₃)—, —CH(CH₃)CH₂—, —(C(CH₃)H₂)₂— and the like. In addition when m equals 3, substituents such as —C(CH₃)₂CH(C₂H₅)—CH₂—, —CH(CH₃)—CH₂—CH(C₂H₅)—, and —CH₂—CH(i-C₃H₇)CH(C₂H₅)— are also contemplated.

The R¹, R² and R³ groups on the amino nitrogen in the compounds of the invention can be the same or different. In some instances as noted above, two of such groups or three of such groups may together represent a heterocyclic ring system with the nitrogen of the amino group being part of such ring, e.g., a monocyclic or bicyclic ring. Examples of suitable —N⁺R¹R²R³ groups include a protonated primary amino group —N⁺H₃; protonated secondary amino groups such as —N⁺H₂(CH₃), —N⁺H₂(—CH₂—CH=CH₂), —N⁺H₂(phenyl), —N⁺H₂(4-pyridyl), etc.; protonated tertiary amino groups such as —N⁺H(CH₃)₂, —N⁺H(CH₂CO₂H)[C(CH₂OH)₃], etc.; quaternary amino groups such as —N⁺(CH₃)₃, —N⁺(CH₃)₂(phenyl) etc.; and protonated tertiary or quaternary, heterocyclic amino groups containing the nitrogen atom in the heterocyclic ring such as pyrrolidinium, 1-methyl pyrrolidinium, piperidinium, 1-methyl piperidinium,

, etc.

As noted above, the compounds of the invention may include one to three Y substituents on the bicyclic ring system. Also, the Q group may include one or two Y substituents. In cases where there is more than one such Y substituent, they may be the same or different. Thus, compounds having combinations of different Y substituents are contemplated within the scope of the invention. Examples of suitable Y substituents include OH, methyl, chloro, bromo, methoxy, cyclohexyl, allyloxy, 2-propynyloxy, hydroxyethyl, methylthio, methylsulfonyl, carboxy, acetoxy, N-methylaminocarbonyl, acetoxymethoxy, acetamido, methylsulfonamido and the like.

Exemplary compounds within the scope of the present invention are:

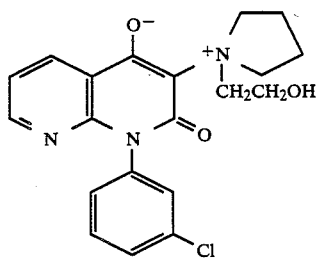 Ia

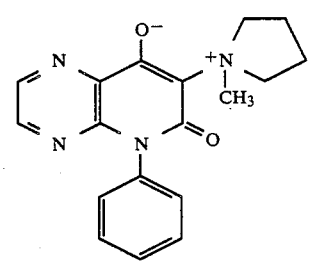 Ib

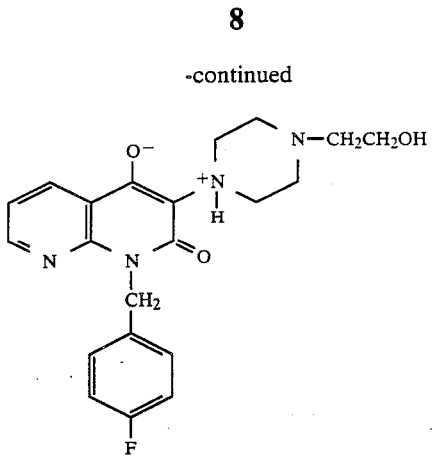 Ic

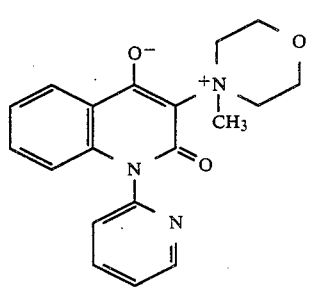 Id

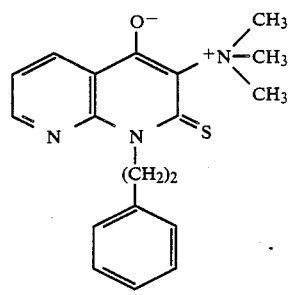 Ie

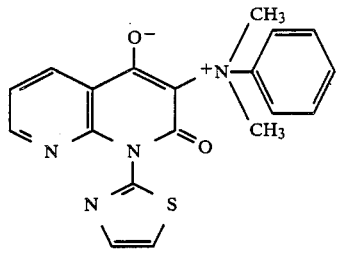 If

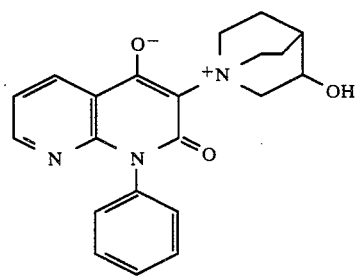 Ig

-continued

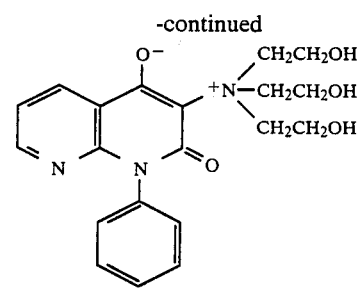 Ih

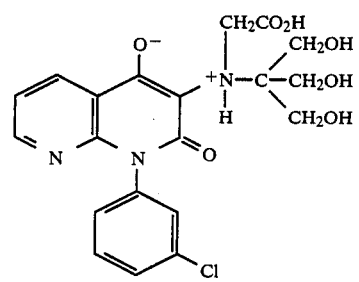

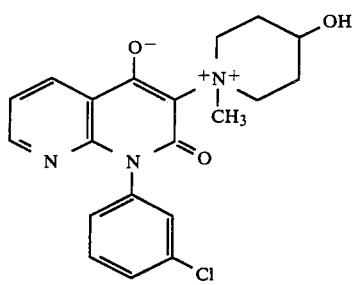 Ij

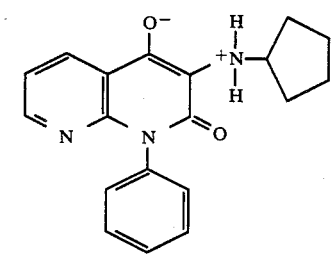 Ik

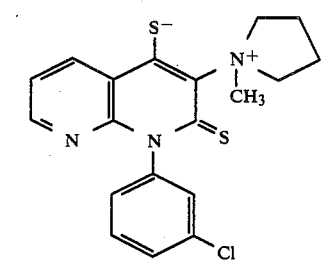 Il

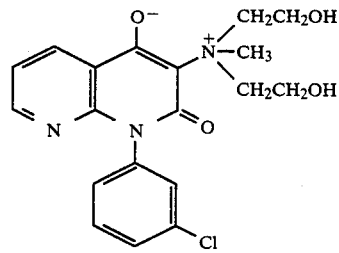 Im

-continued

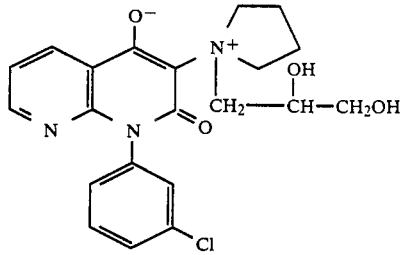 In

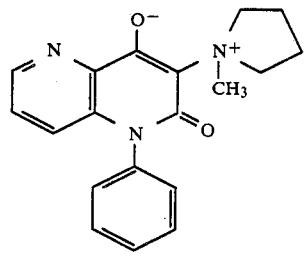 Io

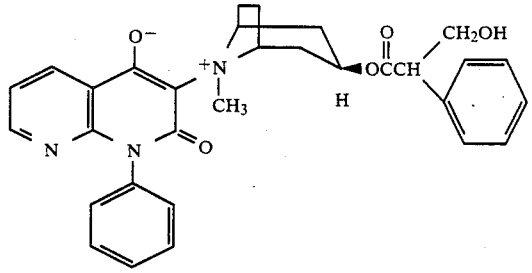 Ip

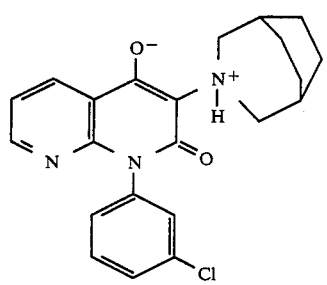 Iq

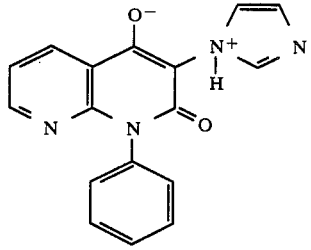 Ir

The compounds of the invention are zwitterionic or inner salts, i.e., they are both positively and negatively charged. However, pharmaceutically acceptable salts of such compounds are also contemplated, i.e., pharmaceutically acceptable acid addition or basic salts. Examples of suitable acid addition salts include the chloride (from hydrochloric acid), methyl sulfate (from methyl sulfuric acid) sulfate (from sulfuric ac:id) and bromide. Basic salts can be formed when at least one of $R^1$, $R^2$ and $R^3$ is H. Examples of suitable basic salts include sodium, potassium or calcium salts (from their corresponding hydroxides).

The compounds of the invention of formula I can exist in unsolvated as well as solvated forms, including hydrated forms, e.g., a hemihydrate. In general, the solvated forms, with pharmaceutically acceptable solvents such as water, ethanol and the like are equivalent to the unsolvated forms for purposes of the invention.

Certain compounds of the invention may exist in isomeric and tautomeric forms. The invention contemplates all such isomers and tautomers—the isomers both in pure form and in admixture, including racemic mixtures.

The compounds of the invention may be employed as anti-allergy agents in the treatment of, for example, asthma, allergic or seasonal rhinitis, and/or chronic bronchitis.

The anti-allergy method of this invention is identified by tests which measure a compound's inhibition of anaphylactic bronchospasm in sensitized guinea pigs having antigen induced broncho-constriction.

In one such test procedure, male Hartley guinea pigs (250–300 g) are sensitized with 5 mg ovalbumin injected i.p. and 5 mg injected s.c. in 1 ml saline on day 1 and 5 mg ovalbumin injected i.p. on day 4. The sensitized animals are used 3–4 weeks later at which time they weigh 450–500 g.

The sensitized guinea pigs are fasted overnight and the following morning are anesthetized with 0.9 ml/kg i.p. of dialurethane (0.1 g/ml diallylbarbituric acid, 0.4 g/ml ethylurea and 0.4 g/ml urethane). The trachea are cannulated and the animals are ventilated by a Harvard rodent respirator at 50 strokes/minute with a stroke volume of 5 ml. A side arm to the tracheal cannula is connected to a Harvard pressure transducer to obtain a continuous measure of intratracheal pressure which is recorded on a Harvard polygraph. The jugular vein is cannulated for the i.v. administration of substances. The animals are challenged with antigen (0.5% ovalbumin) as an aerosol generated from a DeVilbiss Model 65 ultrasonic nebulizer and delivered through the tracheal cannula for 30 seconds. Bronchoconstriction is measured as the peak increase in intratracheal pressure occuring within 5 minutes after antigen challenge.

The sensitized guinea pigs are injected i.v. with 1 mg/kg propranolol, 5 mg/kg indomethacin and 2 mg/kg mepyramine given together in a volume of 1 ml/kg. Fifteen minutes later the animals are challenged with nebulized ovalbumin. Test compounds are administered orally 2 hours before challenge with ovalbumin. Suppression of anaphylactic bronchospasm is expressed as a percent inhibition of the peak increase in intratracheal pressure by comparison to a vehicle-treated control group.

For example, the compound 1-methyl-1-(1,2-dihydro-4-hydroxy-1-phenyl-2-oxo-1,8-naphthyridin-3-yl)-pyrrolidinium-hydroxide, inner salt (Compound A) was found to inhibit anaphylactic bronchospasms in such test procedure when given at an oral dose of 1 mg/kg. This compound was also found to inhibit allergen-induced histamine release from guinea pig and human sensitized tissue. The compounds are effective non-adrenergic, non-anticholinergic, antianaphylactic agents. When administered orally they are active at doses from about 0.1 to 10 mg/kg of body weight; when administered parenterally, e.g., intravenously, the compounds are active at dosages of from about 0.05 to 5 mg/kg body weight, when administered by inhalation (aerosol or nebulizer) the compounds are active at dosages of about 0.25 to 5 mg per puff, one to four puffs may be taken every 4 hours.

The compounds of this invention are also useful for the treatment of inflammation. Thus, they are useful in the treatment of arthritis, bursitis, tendonitis, gout and other inflammatory conditions. The anti-inflammatory use of the compounds of the present invention may be demonstrated by the Reversed Passive Arthus Reaction (RPAR) Synovitis technique as set forth below using male Lewis rats (obtained from Charles River Breeding Laboratories) weighing 200–250 grams and the RPAR Paw technique as also described below. The potency of the compounds is determined using indomethacin as the standard. On the basis of the test results, an oral dosage range of about 5 milligrams per kilogram of body weight per day to about 50 milligrams per kilogram of body weight per day in divided doses taken at about 4 hour intervals is recommended.

The dosage to be administered and the route of administration depends upon the particular compound used, the age and general health of the patient and the severity of the inflammatory condition. Thus, the dose ultimately decided upon must be left to the judgment of a trained health-care practitioner.

RPAR Synovitis Technique

A Lewis rat is dosed orally with drug or placebo one hour prior to intravenous administration of 2.28 mg of bovine serum albumin (BSA) in 0.2 cc of pyrogen-free saline followed by the intraarticular injection of 0.54 mg of rabbit anti-BSA antibody in 0.03 cc of pyrogen-free saline into one knee joint. The contralateral knee is injected with 0.03 cc of pyrogen free saline. All injections are made with the animal under light ether anesthesia. Three hours later the rat is again dosed orally with drug or placebo. All drug doses are split. That is, one-half of the dose is administered before lesion induction and one-half is administered after lesion induction.

The following morning (about 17 hours after lesion induction) the rat is killed and both knee joints are exposed. The subpatellar areolar tissue with attendant synovium is excised and weighed. Differences between the weight of antibody and saline injected knees are considered to represent the inflammatory response for each animal (delta synovial weight). Differences in delta synovial weight between lesion controls and drug-treated rats are evaluated for statistical significance with an analysis of variance. Relative potencies are determined with a linear regression analysis.

Reversed Passive Arthus Response (RPAR) PAW Animals, Materials and Methods

Male Lewis inbred albino rats weighing 180–200 grams obtained from Charles River Breeding Laboratories are used in these experiments. The rats are housed 3 animals/cage and food and water are allowed ad libitum. The animals are numbered 1–3 in each cage and color marked for identification purposes.

Drug and Reagent Preparation

All reagents and drugs are prepared just prior to the study. Crystallized and lyophilized bovine serum albumin (BSA), available from Sigma Chemical Company, is solubilized without shaking in cold, sterile, pyrogen-free saline (10 mg/ml). Lyophilized anti-bovine serum albumin (IgG fraction), obtained from Cappel Laboratories, is suspended in sterile distilled water and diluted with cold, pyrogen-free saline (PFS) just prior to use. The final concentration of anti-bovine serum albumin is 0.5 mg/ml of PFS. Both BSA and anti-BSA solutions are iced during use. Drugs are suspended or solubilized in an aqueous solution of methyl cellulose (MC) with an homogenizer just prior to administration.

Drug Administration and Induction of Inflammation

Groups of animals (6/group) are dosed with drug in MC by gavage once daily for 3 days. The last dose is administered one hour prior to sensitization with BSA. Controls are given MC alone and a drug-standard is usually included in each assay for verification purposes. Drugs are prepared and diluted so as to provide a dose for a 200 gram animal which is equivalent to the mg/kg dose for each experiment. Thus each rat receives an oral dose in a volume of approximately 2.0 cc. One hour after the last dose the animals are lightly anesthetized with ether and "sensitized" by injection of 0.2 ml of PFS containing 1.0 mg of BSA into the penile vein. One hour later, the animals are "challenged" in the right rear paw with subplantar injections of 0.2 ml of PFS containing 0.1 mg of anti-BSA. Immediately after the subplantar injection, the right paw is dipped (up to the lateral maleolus) into the mercury well of a plethysmograph. The volume of mercury displaced is converted to weight and recorded. This value is considered to be the control reading for the animal. Paw volumes are subsequently recorded with a plethysmograph during the development of the inflammation at 2 and 4 hours post-challenge.

Results

Results are expressed by the change in paw volume ($\Delta$ paw volume) from the control reading for each animal to that recorded 2 and 4 hours post-challenge. All drug treated groups are compared to the MC control for significant differences with an analysis of variance. Differences from control in drug-treated groups are expressed as percent change from control. For example, the compound 1-N-methyl-1-(1,2dihydro-4hydroxy-1-phenyl-2-oxo-1,8-naphthyridin-3-yl)-morpholinium-hydroxide, inner salt, hemihydrate and 1-N-methyl-1-(1,2-dihydro-4-hydroxy-1-phenyl-2-oxo-1,8-naphthyridin-3-yl)-pyrrolidinium-hydroxide, inner salt, hemihydrate given at an oral dose of 25 mg/kg, inhibited the paw edema by 86% and 78%, respectively at 2 hours and by 52% and 9%, respectively at 4 hours.

The compounds of this invention are also useful in the treatment of peptic ulcers. They display chemotherapeutic activity which enables them to relieve the symptoms of peptic ulcer disease, stress ulceration, and promote healing of gastric and/or duodenal ulcers. The antiulcer activity of the compounds of this invention is identified by tests which measure the cytoprotective effect in rats. The compounds are also useful as conjunctive therapeutic agents for coadministration with such antiinflammatory/analgesic agents as aspirin, indomethacin, phenylbutazone, ibuprofen, naproxen, tolmetin and other agents. The compounds of this invention prevent the untoward side effects of irritation and damage to the gastrointestinal tract caused by such agents.

The compounds of this invention are evaluated for their antiulcer activity characteristics by standard biological testing procedures such as the indomethacin-induced ulcer and/or ethanol-induced ulcer assays detailed below:

Indomethacin-Induced Ulcer Assay

Male Charles River CD rats (240–260 g) are fasted overnight. The test compound is administered orally in methyl cellulose vehicle (2 ml/kg) to the animals one hour prior to indomethacin 10 mg/kg p.c. The rats are sacrificed by $CO_2$ asphyxiation 4 hours after indomethacin. The stomachs are examined under a magnifying glass for lesions (Chiu et al., *Arch. Int. Pharmacodyn. Ther.*, 270 128, 1984). For instance, Compound A caused a marked reduction of indomethacin-induced ulcers. At 10 mg/kg p.o. ulcer incidence with this compound was 75% in comparison with 100% for the indomethacin control. Moreover, the average lesion size was reduced from 14.6 ($\pm 3.0$) mm in control animals to 1.8 ($\pm 0.5$) mm in drug treated animals, i.e., an 88% reduction in lesion size.

Ethanol-Induced Ulcer Assay

Male Charles River CD rats weighing 250–280 g are fasted and deprived of water for 20 hours before the experiments. The test compound, homogenized in aqueous methyl cellulose vehicle, is administered orally 30 minutes prior to oral administration of 1 ml of absolute ethanol. One hour after ethanol, the rats are sacrificed and the stomachs excised. The stomachs are opened through the greater curvature and the length of each linear hemorrhagic lesion induced by ethanol is measured and summated for each stomach. Results are expressed as the mean lesion length (mm) per rat ($\pm SE$). The data are analyzed by Duncan's multiple range test and a P value of $<0.5$ is considered significant. Compound A at 3mg/kg p.o. reduced the incidence of ulcers from 100% (in controls) to 62%. In addition, the lesion length was reduced from 61.6 ($\pm 8$) mm in the control animals to 6.3 ($\pm 3$) mm in drug treated animals.

The compounds of this invention are found to be effective at doses of about 0.05–50 mg/kg of body weight per day. Preferably the total dosages are administered in 2–4 divided doses per day.

When administered parenterally, e.g. intravenously, the compounds are administered at a dosage range of about 0.01–10 mg/kg of body weight in single or multiple daily doses.

To treat peptic ulcer disease, and prevent and treat drug-induced gastric ulceration, the active compounds of this invention can be administered in unit dosage forms such as tablets, capsules, pills, powders, granules, sterile parenteral solutions or suspensions, suppositories, mechanical delivery devices, e.g. transdermal, and the like.

The compounds of formula I are useful in the treatment of hyperproliferative skin-disease, e.g., psoriasis, which utility may be demonstrated by the Arachidonic Acid Mouse Ear Test described below.

Arachidonic Acid Mouse Ear Test, Materials and Methods

Charles River, female, CD, (SD) BR mice, 6 weeks old, are caged 8/group and allowed to acclimate 1–3 weeks prior to use.

Arachidonic acid (AA) is dissolved in reagent grade acetone (2 mg/.01 ml) and stored at $-20°$ C. for a maximum of 1 week prior to use. Inflammatory reactions are induced by applying 10 $\mu$l of AA to both surfaces of one ear (4 mg total).

Test drugs are dissolved in either reagent grade acetone or aqueous ethanol (only if insoluble in acetone) at the same doses selected by Opas et al., *Fed. Proc.* 43, Abstract 2983, p. 1927 (1984) and Young et al., *J. Invest. Dermatol.* 82, pp 367–371 (1984). These doses are employed to ensure maximum responses and to overcome any difference in topical absorption which could occur with any drug applied in an aqueous ethanol vehicle. The test drug is applied 30 minutes prior to challenge with AA.

The severity of the inflammation is measured as a function of increased ear weight. A 6 mm punch biopsy is removed 1 hour after AA challenge and weighed to the nearest 0.1 mg. Mean ± standard error and all possible comparisons are made via Duncan's Multiple Range Statistic. For instance, Compound A, when tested in the assay at a single dose of 0.5 mg/ear, resulted in a 61% reduction of the severity of inflammation. At a dose of 0.1 mg/ear, the same compound gave a 43% reduction.

When administered for the treatment of hyperproliferative skin disease, the compounds of formula I may be administered topically, orally, rectally or parenterally. When administered topically, the amount of compound administered varies widely with the amount of skin being treated, as well as with the concentration of active ingredient applied to the affected area. When administered orally, the compounds of formula I are effective for the treatment of hyperproliferative skin disease at daily doses ranging from about 0.1 mg/kg to about 100 mg/kg, preferably from about 5 mg/kg to about 50 mg/kg, which may be administered in divided doses. When administered rectally, the compounds of formula I may be administered in daily doses ranging from about 0.1 mg/kg to about 100 mg/kg. When administered parenterally, the compounds of formula I are effective for the treatment of hyperproliferative skin disease in daily doses ranging from about 0.1 mg/kg body weight to about 10 mg/kg body weight which may be administered in divided doses.

As a result of the topical administration of a compound of formula I, a remission of the symptoms of the psoriatic patient, in most cases, can be expected. Thus, one affected by psoriasis can expect a decrease in scaling, erythema, size of the plaques, pruritus and other symptoms associated with psoriasis. The dosage of medicament and the length of time required for successfully treating each individual psoriatic patient may vary, but those skilled in the art of medicine will be able to recognize these variations and adjust the course of therapy accordingly.

Included within the invention are preparations for topical application to the skin whereby the compounds having structural formula I are effective in the treatment and control of skin diseases characterized by rapid rates of cell proliferation and/or abnormal cell proliferation, e.g. psoriasis.

In a preferred method of carrying out the invention, a pharmaceutical formulation comprising a compound of formula I together with a non-toxic, pharmaceutically acceptable topical carrier, usually in concentrations in the range of from about 0.001 percent to about 10 percent, preferably from about 0.1 percent to about 5 percent, is applied several times daily to the affected skin until the condition has improved. Topical applications may then be continued at less frequent intervals (e.g. once a day) to control mitosis in order to prevent return of severe disease conditions.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of the invention may also be deliverable transdermally. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and to the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following examples are intended to illustrate, but not to limit, the present invention.

EXAMPLE 1

Preparation of
4-hydroxy-1-phenyl-1,8-naphthyridin-2(1H)-one

A mixture of methyl-2-phenylamino nicotinate (75.2 g), n-butylacetate (700 mL) and potassium tert-butoxide (148 g) was stirred and heated gradually to reflux. The mixture was refluxed for 16 hours, after which time it was cooled and poured into water (7 L) with stirring. The resulting mixture was acidified to pH 5 with concentrated HCl when a white solid precipitated. The product was filtered off and air dried. The solid product was then suspended in hexane (3 L), triturated, filtered and washed with fresh hexane. This purification process was repeated using ether (1.5 L). The product was dried to yield 48 g of the desired product, m.p. 312°–314° C.

By a similar procedure, using modifications well known to one skilled in the art, the starting materials
ethyl-2-(pyrazinylamino)-nicotinate,
ethyl-2-(4-pyrimidinylamino)-nicotinate,
ethyl-2-(3-(1,2,4-triazinylamino))-nicotinate, and
ethyl-2-(2-thienylmethylamino)-nicotinate
can to converted to
4-hydroxy-1-(2-pyrazinyl)-1,8-naphthyridin-2(1H)-one,
4-hydroxy-1-(4-pyrimidinyl)-1,8-naphthyridin-2(1H)-one,
4-hydroxy-1-(3-(1,2,4-triazinyl))-1,8-naphthyridin-2(1H)-one, and
4-hydroxy-1-(2-thienylmethyl)-1,8-naphthyridin-2(1H)-one, respectively.

EXAMPLE 2

Preparation of
3-bromo-4-hydroxy-1-phenyl-1,8-naphthyridin-2(1H)-one

To a suspension of 4-hydroxy-1-phenyl-1,8-naphthyridin-2(1H)-one (1 g) in $CH_2Cl_2$ (20 mL) was added, dropwise and with stirring, a solution of bromine (0.7 g) in $CH_2Cl_2$ (5 mL). The mixture was stirred at room temperature overnight, after which time the product was filtered off, dried in air and recrystallized from acetonitrile to yield 0.87 g of the product, m.p. 280° C.

By employing a similar procedure to that described in Example 2 above using simple modifications based on practices well-known to one skilled in the art, the compounds
4-hydroxy-1-(2-pyrazinyl)-1,8-naphthyridin-2(1H)-one,
4-hydroxy-1-(4-pyrimidinyl)-1,8-naphthyridin-2(1H)-one,
4-hydroxy-1-(3-(1,2,4-triazinyl))-1,8-naphthyridin-2(1H)-one, and
4-hydroxy-1-(2-thienylmethyl)-1,8-naphthyridin-2(1H)-one
can be converted to
3-bromo-4-hydroxy-1-(2-pyrazinyl)-1,8-naphthyridin-2(1H)-one,
3-bromo-4-hydroxy-1-(4-pyrimidinyl)-1,8-naphthyridin-2(1H)-one,
3-bromo-4-hydroxy-1-(3-(1,2,4-triazinyl))-1,8-naphthyridin-2(1H)-one, and
3-bromo-4-hydroxy-1-(2-thienylmethyl)-1,8-naphthyridin-2(1H)-one, respectively.

EXAMPLE 3

Preparation of
1-(1,2-dihydro-4-hydroxy-1-phenyl-2-oxo-1,8-naphthyridin-3-yl)-1-methyl-pyrrolidinium hydroxide, inner salt In dry pyridine (30 mL), 3-bromo-4-hydroxy-1-phenyl-1,8-naphthyridin-2(1H)-one (10 g) was suspended. N-methyl pyrrolidine (20 mL) was added to the suspension. The mixture was heated to 95°–100° C. with stirring, and was kept there for about 33 hours. The product was evaporated under high vacuum to provide a dark oil. This oil was slurried with 200 mL of $CH_3CN(40)$: $H_2O(60)$: $CH_3CO_2H(1)$ and filtered. The solid residue on the filter was rinsed with water and the filtrate was evaporated to remove most of the $CH_3CN$. Reversed phase chromatography through an E. Merck RP-8 LoBar column, eluting with increasing concentrations of $CH_3CN$ in $H_2O$ (containing 1% $CH_3CO_2H$) gave a moderately pure product which was subjected to a second chromatographic separation using the same conditions as above. Fractions containing the product were combined and evaporated to yield a solid which was recrystallized from $CH_2Cl_2$/isopropanol to yield the desired product, m.p. 245°–250° C.

EXAMPLE 4

Preparation of
1-(1,2-dihydro-4-hydroxy-1-phenyl-2-oxo-1,8-naphthyridin-3-yl)-1-methyl-pyrrolidinium chloride 1-(1,2-dihydro-4-hydroxy-1-phenyl-2-oxo-1,8-naphthyridin-3-yl)-1-methyl-pyrrolidinium hydroxide, inner salt (0.1 g) was dissolved in 0.1 N-HCl solution (38 mL). The solution was concentrated under high vacuum to provide an oil which crystallized on the addition of isopropanol. The solid was filtered off and washed with isopropanol to yield the desired hydrochloride salt, m.p. 195° C.

EXAMPLE 5

Preparation of 1-(1,2-dihydro-4-hydroxy-1-phenyl-2-oxo-1,8-naphthyridin-3-yl)-pyrrolidinium hydroxide, inner salt A solution of 3-bromo-4-hydroxy-1-phenyl-1,8-naphthyridin-2(1H)-one (2 g) in a mixture of pyrrolidine (10 mL) and DMF (5 mL) was stirred and heated at 100° C. for 2 days. The resulting mixture was then cooled, diluted with $CH_2Cl_2$ (100 mL) and filtered. The solid was triturated with hot $CHCl_3$, filtered, and dried to yield the desired product, m.p. 282°–284° C.

Some of the product was purified by (1) dissolving in a minimum volume of 2,2,2-trifluoroethanol and (2) precipitating by the addition of 4 volumes of methanol. The pure product charred and decomposed when heated above 285° C.

EXAMPLE 6

Preparation of 1-(1,2-dihydro-4-hydroxy-1-phenyl-2-oxo-1,8-naphthyridin-3-yl)-4-hydroxy-piperidinium hydroxide, inner salt A solution of 3-bromo-4-hydroxy-1-phenyl-1,8-naphthyridin-2(1H)-one (1 g) in a mixture of 2,6-lutidine (5 mL) and 4-hydroxy-piperidine (3.12 g) was heated at 100° C. for 32 hours. The lutidine was removed by evaporation under high vacuum. The residue was dissolved in $CH_3CN(20):H_2O(80):CH_3CO_2H(1)$ and separated by reversed phase preparative HPLC (Whatman Magnum 40 with Partisil 40/ODS-3). The fractions containing the desired product were combined and evaporated to yield a partially crystalline material which was recrystallized from isopropanol to yield the desired product, m.p. 256°–258° C.

The following compounds were also prepared by the techniques similar to those described above:

1-(1,2-dihydro-4-hydroxy-1-phenyl-2-oxo-1,8-naphthyridin-3-yl)quinuclidinium hydroxide, inner salt, hemihydrate, m.p. 290° C.

1-methyl-1-(1,2-dihydro-4-hydroxy-1-phenyl-2-oxo-1,8-naphthyridin-3-yl)-morpholinium hydroxide, inner salt, hemihydrate, m.p. 248°–249° C.

1-(1,2-dihydro-4-hydroxy-1-phenyl-2-oxo-1,8-naphthyridin-3-yl)-piperidinium hydroxide, inner salt, hemihydrate, m.p. 261°–263° C. (decomp.).

1-(1,2-dihydro-4-hydroxy-1-phenyl-2-oxo-1,8-naphthyridin-3-yl)-2-hydroxymethyl piperidinium hydroxide, inner salt, hemihydrate, m.p. 135°–138° C.

By employing procedures similar to those described above in Examples 3, 4, 5 and 6 with simple modifications well known to one skilled in the art, the compounds 3-bromo-4-hydroxy-1-(2-pyrazinyl)-1,8- naphthyridin-2(1H)-one, 3-bromo-4-hydroxy-1-(4-pyrimidinyl)-1,8- naphthyridin-2(1H)-one, 3-bromo-1-(3-chlorophenyl)-4-hydroxy-1,8-naphthyridin-2(1H)-one, 3-bromo-4-hydroxy-1-(3-(1,2,4-triazinyl))-1,8-naphthyridin-2(1H)-one, and 3-bromo-4-hydroxy-1-(2-thienylmethyl)-1,8-naphthyridin-2(1H)-one can be converted to 1-[1,2-dihydro-4-hydroxy-2-oxo-1-(2-pyrazinyl)-1,8-naphthyridin-3-yl]-1-methyl-pyrrolidinium hydroxide, inner salt, 1-[1,2-dihydro-4-hydroxy-2-oxo-1-(4-pyrimidinyl)-1,8-naphthyridin-3-yl]-1-methylpiperidinium hydroxide, inner salt, 1-[1-(3-chlorophenyl)-1,2-dihydro-4-hydroxy-2-oxo-1,8-naphthyridin-3-yl]-1-methyl- pyrrolidinium hydroxide, inner salt, or 1-[1-(3-chlorophenyl)-1,2-dihydro-4-hydroxy-2-oxo-1,8-naphthyridin-3-yl]-piperidinium hydroxide, inner salt, m.p. 258.5°–261° C.

1-[1,2-dihydro-4-hydroxy-2-oxo-1-(3-(1,2,4- triazinyl))-1,8-naphthyridin-3-yl]- pyrrolidinium hydroxide, inner salt, and 1-(1,2-dihydro-4-hydroxy-2-oxo-1-(2- thienylmethyl)-1,8-naphthyridin-3-yl]-piperidinium hydroxide, inner salt, respectively.

EXAMPLE 7

Preparation of 1-(1,2-dihydro-4-hydroxy-1-phenyl-2-oxo-1,8-naphthyrindin-3-yl)-pyrrolidinium hydroxide, inner salt Step A: To a stirred solution of 25.45 g (0.11 M) of methyl-2-phenylamino-nicotinate in 160 mL of t-butyl methyl ether (tBuOMe) (dried over 3A° sieves) heated to 50° (under $N_2$) 19.5 mL (2.2×0.11 M) of hloroacetylchloride followed by 31 mL (4×0.11 M) of propylene oxide was added. The reaction mixture was heated at 50° C. for 1.5 hours and then 300 mL tBuOMe was added. This solution (cooled to room temperature) was washed with 200 mL $H_2O$ containing 9.37 g (0.11 M) of $NaHCO_3$ followed by 30 mL of saturated aqueous NaCl solution. At this stage the product that crystallized out was dissolved in 100 mL $CH_2Cl_2$ and this $CH_2Cl_2$ was mixed with tBuOMe solution. The solution, as is, was used for the next reaction.

Step B: To the above solution at room temperature under $N_2$, 37.2 mL (4×0.11 M) of pyrrolidine was added and this solution was gently refluxed overnight. 9.3 mL (0.11 M) of pyrrolidine was added, and the reaction was refluxed for an additional two hours. This mixture was diluted with 600 mL tBuOMe and washed with 300 mL $H_2O$ and the aqueous layers were back extracted with 200 mL tBuOMe. The combined organic (tBuOMe) layer was washed with 150 mL saturated aqueous NaCl soln., dried over anhydrous $Na_2SO_4$, and then concentrated in vacuum (oil pump vacuum) to 64.6 g of a crude brown semisolid, which was the methyl ester of 2-[1-pyrrolidinyl acetyl]phenylamino]-3-pyridine carboxylic acid.

Step C: The solid from step B above was suspended in 600 mL of cold (0° C.) tBuOMe (dried over 3A° sieves) under $N_2$. To this cold stirred mixture, 27.5 g (2.2×0.11 M) potassium t-butoxide was added, the reaction mixture was stirred for 1 hour, and then it was quenched with 15 mL (2.4×0.11 M) of glacial acetic acid.

The stirred reaction mixture was allowed to attain room temperature and then 350 mL $H_2O$ was added to it. The resultant solid was filtered, washed with tBuOMe, $H_2O$, a small amount of $CH_2Cl_2$, acetone, and then air dried to obtain 27.09 g of the white product 1-(1,2-dihydro-4-hydroxy-1-phenyl-2-oxo-1,8-naphthyridin-3-yl)-pyrrolidinium hydroxide, inner salt. The crude product was crystallized from 300 mL $CH_3OH+16$ mL conc. $H_2SO_4$ at 50° C.+3 g carbon;

filtered, diluted with 575 mL H₂O, cooled to 0° C. and filtered; and draft oven dried at 60° C. for about 18 hours to give 22.2 g (82%) of crystallized white product.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A pharmaceutical composition useful for treating allergic reactions, inflammation, peptic ulcers and/or hyperproliferative skin disease comprising an antiallergic, antiinflammatory, cytoprotective and/or anti-hyperproliferative effective amount of a compound having the structural formula I

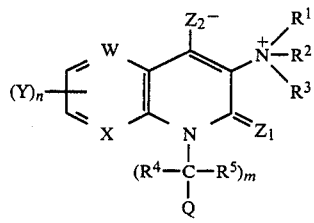

or a pharmaceutically acceptable salt or solvate thereof, in combination with a pharmaceutically acceptable carrier wherein:

W and X may be the same or different and each independently represents —CH= or —N=;

$Z_1$ and $Z_2$ are the same or different and each independently represents O or S;

$R^1$, $R^2$, $R^3$, $R^4$ and $R^5$ are the same or different and each may be independently selected from the group consisting of H, alkyl having from 1 to 12 carbon atoms, alkenyl having from 3 to 8 carbon atoms, alkynyl having from 3 to 8 carbon atoms, alkoxyalkyl having from 1 to 6 carbon atoms in the alkoxy portion and from 2 to 6 atoms in the alkyl portion thereof, hydroxyalkyl having from 2 to 8 carbon atoms, cycloalkyl having from 3 to 8 carbon atoms, acyloxyalkyl having from 1 to 6 carbon atoms in the acyloxy portion and from 2 to 8 carbon atoms in the alkyl portion thereof, and —R⁶—CO₂Rᴼ wherein $R^6$ represents an alyklene group having from 1 to 6 carbon atoms and $R^O$ represents hydrogen or an alkyl group having from 1 to 6 carbon atoms, with the provisos that the OH of the hydroxyalkyl group and the acyloxy of the acyloxyalkyl group are not joined to the same carbon atom as another heteroatom, that at least one of $R^1$, $R^2$ and $R^3$ is not hydrogen and that, when $R^1$, $R^2$ and/or $R^3$ are alkenyl or alkynyl, there is at least one carbon-carbon single bond between the nitrogen atom and the carbon-carbon double or triple bond;

in addition, one of $R^1$, $R^2$ or $R^3$ can be an aryl group containing 6 to 15 carbon atoms or an aromatic heterocyclic group containing 3 to 14 carbon atoms, either of which can be substituted with one to three substituents Y as defined below;

in further addition, two of $R^1$, $R^2$ adn $R^3$ can be joined together to represent an imidazolyl ring or to represent a ring which can contain from 2 to 8 carbon atoms, said ring optionally containing a —O—, —S— and/or —NR⁴— heteroatomic group (wherein $R^4$ is as defined above) and/or optionally containing a carbon-carbon double bond, and said ring optionally being substituted with one to three additional substituents $R^7$ which substituents may be the same or different and are each independently selected from OH with the proviso that OH is not on a carbon already joined to a hetero atom, —O—acyl having from 1 to 6 carbon atoms, hydroxyalkyl having from 1 to 8 carbon atoms, alkoxyalkyl having from 1 to 6 carbon atoms in each alkyl portion thereof, alkyl having from 1 to 6 carbon atoms, alkenyl having from 3 to 8 carbon atoms, alkynyl having from 3 to 8 carobn atoms, —COOR¹⁰ wherein $R^{10}$ is H, alkyl or aryl containing from 6-15 carbon atoms, or any two $R^7$ substituent groups may represent a hydrocarbon ring having from 4 to 8 total carbon atoms;

in still further addition, all three of $R^1$, $R^2$, and $R^3$ can be joined together to represent a polycyclic ring, which polycyclic ring can optionally be substituted by one to three substituents groups $R^7$ as defined above;

m is an integer of from 0 ot 3;

n is an integer of from 0 to 3;

Q represents an aryl group containing 6 to 15 carbon atoms or an aromatic heterocyclic group containing 3 to 14 carbon atoms, either of which group can optionally be substituted with 1 to 3 substituents Y as define below;

each Y substituent is independently selected from the group consisting of hydroxy, alkyl having from 1 to 6 carbon atoms, halogen, NO₂, alkoxy having from 1 to 6 carbon atoms, trifluoromethyl, cyano, cycloalkyl having from 3 to 7 carbon atoms, alkenyloxy having from 3 to 6 carbon atoms, alkynyloxy having 3 to 6 carbon atoms, hydroxyalkyl having from 1 to 6 carbon atoms, —S(O)ₙ—R⁸ (wherein $R^8$ represents aklyl having from 1 to 6 carbon atoms and n is as defined above), —SO₂NH₂, —CO—R⁹ (wherein $R^9$ represents OH, —NH—R⁸ or —O—R⁸, where $R^8$ is as defined above), —O—B—COR⁹ (wherein B represents an alkylene group having from 1 to 4 carbon atoms and $R^9$ is as defined above), —NH₂, —NHCHO, —NH—CO—R⁹ (wherein $R^9$ is as defined above, with the proviso that it is not hydroxy), —NH—COCF₃, —NH—SO₂R⁸ (wherein $R^8$ is as defined above), and —NHSO₂CF₃.

2. A composition according to claim 1, wherein in the compound of formula I at least one of W and X is —N=.

3. A composition according to claim 1, wherein in the compound of formula I X is —N= and W is —CH=.

4. A composition according to claim 3, wherein in the compound of formula I at least one of $Z_1$ and $Z_2$ is O.

5. A composition according to claim 4, wherein in the compound of formula I $Z_1$ and $Z_2$ both are O.

6. A composition according to claim 5, wherein in the compound of formula I n is 0.

7. A composition according to claim 6, wherein in the compound of formula I m is 0.

8. A composition according to claim 7, wherein in the compound of fromula I Q is an aryl group, which may optionally be substituted with one or two Y groups.

9. A composition according to claim 8, wherein in the compound of formula I Q is a phenyl group, which may optionally be substituted with one or two Y groups.

10. A pharmaceutical composition useful for treating one or more diseases selected from allergic reactions, inflammation, peptic ulcers and hyperproliferative skin disease comprising an antiallergic, antiinflammatory, cytoprotective and/or anti-hyperproliferative effective amount of a compound selected from:

1-(1,2-dihydro-4-hydroxy-1-phenyl-2-oxo-1,8-naphthyridin-3-yl)-1-methyl-pyrrolidinium hydroxide, inner salt;

I-(1,2-dihydro-4-hydroxy-1-phenyl-2-oxo-1,8-naphthyridin-3-yl)-pyrrolidinium hydroxide, inner salt;

1-(1,2-dihydro-4-hydroxy-1-phenyl-2-oxo-1,8-naphthyridin-3-yl)-4-hydoxy-piperidinium hydroxide, inner salt;

1-(1,2-dihydro-4-hydroxy-1-phenyl-2-oxo-1,8-naphthyridin-3-yl)-quinuclidinium hydroxide, inner salt;

1-(2-dihydro-4-hydroxy-1-phenyl-2-oxo-1,8-naphthyridin-3-yl)-1-methyl-morpholinium hydroxide, inner salt;

1-(1,2-dihydro-4-hydroxy-1-phenyl-2-oxo-1,8-naphthyridin-3-yl)-piperidinium hydroxide, inner salt; or 1-(1,2-dihydro-4-hydroxy-1-phenyl-2-oxo-1,8-naphthyridin-3-yl)-2-hydroxymethyl-piperidinium hydroxide, inner salt; or pharmaceutically acceptable salts thereof in combination with a pharmaceutically acceptable carrier.

11. A pharmaceutical composition useful for treating one or more diseases selected from allergic reactions, inflammation, peptic ulcers and hyperproliferative skin disease comprising an antiallergic, antiinflammatory, cytoprotective and/or anti-hyperproliferative effective amount of 1-(1,2-dihydro-4-hydroxy-1-phenyl-2-oxo-1,8-naphthyridin-3-yl)-1-methyl-pyrrolidinium hydroxide, inner salt or a pharmaceutically acceptable salt or solvate thereof, in combination with a pharmaceutically acceptable carrier.

12. A pharmaceutical composition useful for treating one or more diseases selected from allergic reactions, inflammation, peptic ulcers and hyperproliferative skin disease comprising an antiallergic, antiinflammatory, cytoprotective and/or anti-hyperproliferative effective amount of 1-(1,2-dihydro-4-hydroxy-1-phenyl-2-oxo-1,8-naphthyridin-3-yl)-pyrrolidinium hydroxide, inner salt or a pharmaceutically acceptable salt or solvate thereof in combination with a pharmaceutically acceptable carrier.

13. A method for treating allergic reactions in a mammal which comprises administering to said mammal an anti-allergic effective amount of a pharmaceutical composition containing as an active ingredient a compound having the structural formula I

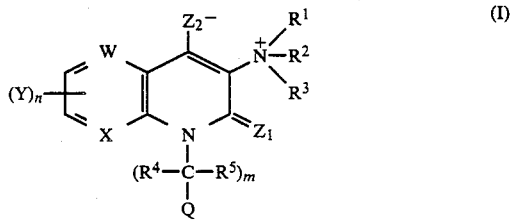

(I)

or a pharmaceutically acceptable salt or solvate thereof, wherein:

W and X may be the same or diffrenet and each independently represents —CH= or —N=;

$Z_1$ and $Z_2$ are the same or differnet and each independently represents 0 or S;

$R^1$, $R^2$, $R^3$, $R^4$ and $R^5$ are the same or different and each may be independently selected from the group consisting of H, alkyl having from 1 to 12 carbon atoms, alkenyl having from 3 to 8 carbon atoms, alkynyl having from 3 to 8 carbon atoms, alkoxyalkyl having from 1 to 6 carbon atoms in the alkoxy portion and from 2 to 6 atoms in the alkyl portion thereof, hydroxyalkyl having from 2 to 8 carbon atoms, cycloalkyl having from 3 to 8 carbon atoms, acyloxyalkyl having from 1 to 6 carbon atoms in the acyloxy portion and from 2 to 8 carbon atoms in the alkyl portion thereof, and —$R^6$—$CO_2R^O$ wherein $R^6$ represents an alyklene group having from 1 to 6 carbon atoms and $R^0$ represents hydrogen or an alkyl group having from 1 to 6 carbon atoms, with the provisos that the OH of the hydroxyalkyl group and the acyloxy of the acyloxyalkyl group are not joined to the same carbon atom as another heteroatom, that at least one of $R^1$, $R^2$, and $R^3$ is not hydrogen, and that when $R^1$, $R^2$ and/or $R^3$ are alkenyl or alkynyl, there is at least one carbon-carbon single bond between the nitrogen atom and carbon-carbon double or triple bond;

in addition, one of $R^1$, $R^2$ or $R^3$ can be can an aryl group containing 6 to 15 carbon atoms or an aromatic heterocyclic group containing 3 to 14 carbon atoms, either of which can be substituted with one to three substitutents y as defined below;

in further addition, two of $R^1$, $R^2$ and $R^3$ can be joined together ot represent an imidazolyl ring or to represent a ring which can contain from 2 to 8 carobn atoms, said ring optionally containing a —O—, —S— and/or —$NR_4$— heteroatomic group (wherein $R^4$ is as defined above) and/or optionally containing a carbon-carbon double bond, and said ring optionally being substituted with one to three additional substituents $R^7$ which substitutents may be the same or different and are each independently selected from OH with the proviso that OH is not on a carbon already joined to a hetero atom, -O-acyl having from 1 to 6 carbon atoms, hydroxyalkyl having from 1 to 8 carbon atoms, alkoxyalkyl having from 1 to 6 carbon atoms in each alkyl portion thereof, alkyl having from 1 to 6 carbon atoms, alkenyl having from 3 to 8 carbon atoms, alkynyl having from 3 to 8 carbon atoms, —$COOR^{10}$ wherein R 10 is H, alkyl or aryl containing from 6–15 carbon atoms, or any two $R^7$ substituent groups may represent a hydrocarbon ring having from 4 to 8 total carbon atoms;

in still further addition, all three of $R^1$, $R^2$, and $R^3$ can be joined together to represent a polycyclic ring, which polycyclic ring can optionally be substittued by one to three substituents groups $R^7$ as defined above;

m is an integer of from 0 to 3;

n is an integer of from 0 to 2;

Q represents an aryl group containing 6 to 15 carbon atoms or an aromatic hetrocylcic group containing 3 to 14 carbon atoms, either of which group can optionally be substituted with 1 to 3 substituents Y as defined below;

each Y substituent is independently selected from the group consisting of hydroxy, alkyl having from 1 to 6 carbon atoms, halogen, $NO_2$, alkoxy having from 1 to 6 carbon atoms, trifluoromethyl, cyano, cycloalkyl having from 3 to 7 carbon atoms, akenyloxy having from 3 to 6 carbon atoms, alkynyloxy having 3 to 6 carbon atoms, hydroxyalkyl having from 1 to 6 carbon atoms, $-S(O)_n-R^8$ (wherein $R^8$ represents akyl having from 1 to 6 carbon atoms and n is as defined above), $-SO_2NH_2$, $-CO-R^9$ (wherein $R^9$ represents OH, $-NH-R^8$ or $-O-R^8$, where $R^8$ is as defined above), $-O-B-COR^9$ (wherein B represents an alkylene group having from 1 to 4 carbon atoms and $R^9$ is as defined above), $-NH_2$, $-NHCHO$, $-NH-CO-R^9$ (wherein $R^9$ is as defined above, with the proviso that it is not hydroxy), $-NH-COCF_3$, $-NH-SO_2R^8$ (wherein $R^8$ is as defined above), and $-NHSO_2CF_3$.

14. A method for treating inflammation in a mammal which comprises administering to said mammal an antiinflammatory effective amount of a pharmaceutical composition containing as an active igredient a compound having the structural formula I

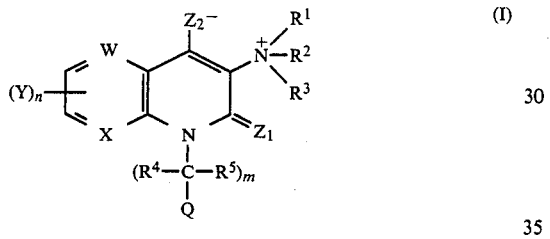

or a pharmaceutically acceptable salt or solvate thereof, wherein:

W and X may be the same or different and each independently represents $-CH=$ or $-N=$;

$Z_1$ and $Z_2$ are the same or different and each independently represents O or S;

$R^1$, $R^2$, $R^3$, $R^4$ and $R^5$ are the same or different and each may be independently selected from the group consisting of H, alkyl having from 1 to 12 carbon atoms, alkenyl having from 3 to 8 carbon atoms, alkynyl having from 3 to 8 carbon atoms, alkoxyalkyl having from 1 to 6 carbon atoms in the alkoxy portion and from 2 to 6 atoms in teh alkyl portion thereof, hydroxyalkyl having from 2 to 8 carbon atoms, cycloalkyl having from 3 to 8 carbon atoms, acyloxyalkyl having from 1 to 6 carbon atoms in the acyloxy portion and from 2 to 8 carbon atoms in the alkyl portion thereof, and $-R^6-CO_2R^0$ wherein $R^6$ represents an alyklene group having form 1 to 6 carbon atoms and $R^0$ rerpesents hydrogen or an alkyl group having from 1 to 6 carbon atoms, with the provisos that the OH of the hydroxyalkyl group and the acyloxy of the acyloxyalkyl group are not joined to the same carbon atom as another heteroatom and that when $R^1$, $R^2$ and/or $R^3$ are alkenyl or alkynyl, there is at least one carbon-carbon single bond between the nitrogen atom and the carbon-carbon double or triple bond;

in addition, one of $R^1$, $R^2$ or $R^3$ can be an aryl group containing 6 to 15 carbon atoms or an aromatic heterocyclic group containing 3 to 14 carbon atoms, either of which can be substituted with one to three substituents Y as defined below;

in further addition, two of $R^1$, $R^2$ and $R^3$ can be joined together to represent an imidazolyl ring or to represent a ring which can contain from 2 to 8 carbon atoms, said ring optionally containing a $-O-$, $-S-$ and/or $-NR^4-$ heteroatomic group (wherein $R^4$ is as defined above) and/or optionally containing a carbon-carbon double bond, and said ring optionally being substituted with one to three additional substituents $R^7$ which substitutuents may be the same or differnet and are each independently selected from OH with the proviso that OH is not on a carbon already joined to a hetero atom, $-O-$acyl having from 1 to 6 carbon atoms, hydroxyalkyl having from 1 to 8 carbon atoms, alkoxyalkyl having from 1 to 6 carbon atoms in each alkyl portion thereof, alkyl having from 1 to 6 carbon atoms, alkenyl having from 3 to 8 carbon atoms, alkynyl having from 3 to 8 carbon atoms, $-COOR^{10}$ wherein $R^{10}$ is H, alkyl or aryl containing from 6-15 carbon atoms, or any two $R^7$ substituent groups may represent a hydrocarbon ring having from 4 to 8 total carbon atoms;

in still further addition, all three of $R^1$, $R^2$ and $R^3$ can be joined together to represent a polycylic ring, which polycyclic ring can optionally be substituted by one to three substituents groups $R^7$ as deifned above;

m is an integer of from 0 to 3;

n is an integer of from 0 to 2;

Q represents an aryl group containing 6 to 15 carbon atoms or an aromatic heterocyclic group containing 3 to 14 carbon atoms, either of which group can optionally be substituted with 1 to 3 subsitutents Y as defined below;

each Y substituent is independently selected from the group consisting of hydroxy, alkyl having from 1 to 6 carbon atoms, halogen, $NO_2$, alkoxy having from 1 to 6 carbon atoms, trifluoromethyl, cyano, cycloalkyl having from 3 to 7 carbon atoms, alkenyloxy having from 3 to 6 carbon atoms, alkynyloxy having 3 to 6 carbon atoms, hydroxyalkyl having from 1 to 6 carbon atoms, $-S(O)_n-R^8$ (wherein $R^8$ represents alkyl having from 1 to 6 carbon atoms and n is as defined above), $-SO_2NH_2$, $-CO-R^9$ (wherein $R^9$ represents OH, $-NH-R^8$ or $-O-R^8$, where $R^8$ is as defined above), $-O-B-COR^9$ (wherein B represents an alkylene group having from 1 to 4 carbon atoms and $R^9$ is as defined above), $-NH_2$, $-NHCHO$, $-NH-CO-R^9$ (wherein $R^9$ is as defined above, with the proviso that it is not hydroxy), $-NH-COCF_3$, $-NH-SO_2R^8$ (wherein $R^8$ is as defined above), and $-NHSO_2CF_3$.

15. A method for treating peptic ulcers in a mammal which comprises administering to said mammal a cytoprotective amount of a pharmaceutical composition containing as an active ingredient a compound having the structural formula

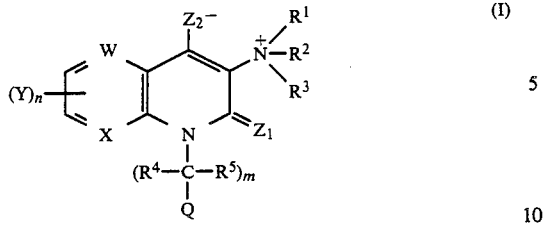

or a pharmaceutically acceptable salt or solvate thereof, wherein:

W and X may be the same or different and each independently represents —CH= or —N=;

$Z_1$ and $Z_2$ are the same or different and each independently represents O or S;

$R^1$, $R^2$, $R^3$, $R^4$, and $R^5$ are the same or different and each may be independently selected from the group consisting of H, alkyl having from 1 to 12 carbon atoms, alkenyl having from 3 to 8 carbon atoms, alkynyl having from 3 to 8 carbon atoms, alkoxyalkyl having from 1 to 6 carbon atoms in the alkoxy portion and from 2 to 6 atoms in the alkyl portion thereof, hydroxyalkyl having from 2 to 8 carbon atoms, cycloalkyl having from 3 to 8 carbon atoms, acyloxyalkyl having from 1 to 6 carbon atoms in the acyloxy portion and from 2 to 8 carbon atoms in the alkyl portion thereof, and —$R^6$—$CO_2R^0$ wherein $R^6$ represents an alyklene group having from 1 to 6 carbon atoms and $R^0$ represents hydrogen or an alkyl group having from 1 to 6 carbon atoms, with the provisos that the OH of the hydroxyalkyl group and the acyloxy of the acyloxyalkyl group are not joined to the same carbon atom as another heteroatom and that when $R^1$, $R^2$ and/or $R^3$ are alkenyl or alkynyl, thereis at least one carbon-carbon single bond between the nitrogen atom and the carbon-carbon double or triple bond;

in addition, one of $R^1$, $R^2$ or $R^3$ can be an aryl group containing 6 to 15 carbon atoms or an aromatic heterocyclic group containing 3 to 14 carbon atoms, either of which can be substituted with one to three substituents Y as defined below;

in further addition, two of $R^1$, $R^2$ and $R^3$ can be joined together to represent an imidazolyl ring or to represent a ring which can contain from 2 to 8 carbon atoms, said ring optionally containing a —O—, —S— and/or —$NR^4$— heteroatomic group (wherein $R^4$ is as defined above) and/or optionally containing a carbon-carbon double bond, and said ring optionally being substituted with one to three additional substituents $R^7$ which substituents may be the same or different and are each independently selected from OH with the proviso that OH is not on a carbon already joined to a hetero atom, —O-acyl having from 1 to 6 carbon atoms, hydroxyalkyl having form 1 to 8 carbon atoms, alkoxyalkyl having from 1 to 6 carbon atoms in each alkyl portion thereof, alkyl having from 1 to 6 carbon atoms, alkenyl having from 3 to 8 carbon atoms, alkynyl having from 3 to 8 carbon atoms, —$COOR^{10}$ wherein $R^{10}$ is H, alkyl or aryl containing from 6-15 carbon atoms, or any two $R^7$ substituent groups may represent a hydrocarbon ring having from 4 to 8 total carbon atoms;

in still further addition, all three of $R^1$, $R^2$ and $R^3$ can be joined together to represent a polycyclic ring, which polycyclic ring can optionally be substituted by one to three substituents groups $R^7$ as defined above;

m is an integer of from 0 to 3;

n is an integer of from 0 to 2;

Q represents an aryl group containing 6 to 15 carbon atoms or an aromatic heterocyclic group containing 3 to 14 carbon atoms, either of which group can optionally be substituted with 1 to 3 substituents Y as defined below;

each Y substituent is indnependently selected from the group consisting of hydroxy, alkyl having from 1 to 6 carbon atoms, halogen, $NO_2$, alkoxy having from 1 to 6 carbon atoms, trifluoromethyl, cyano, cycloalkyl having from 3 to 7 carbon atoms, alkenyloxy having from 3 to 6 carbon atoms, alkynyloxy having 3 to 6 carbon atoms, hydroxyalkyl having from 1 to 6 carbon atoms, —$S(O)_n$—$R^8$ (wherein $R^8$ represents alkyl having from 1 to 6 carbon atoms and n is as defined above), —$SO_2NH_2$, —CO—$R^9$ (wherein $R^9$ represents OH, —HN—$R^8$ or —O—$R^8$, where $R^8$ is as defined above), —O—B—$COR^9$ (wherein B represents an alkylene group having from 1 to 4 carbon atoms and $R^9$ is as defined above), —$NH_2$, —NHCHO, —NH—CO—$R^9$ (wherein $R^9$ is as defined above, with the proviso that it is not hydroxy), —NH—$COCF_3$, —NH—$SO_2R^8$ (wherein $R^8$ is as defined above), and —$NHSO_2CF_3$.

16. A method for treating a mammal suffering from hyperproliferative skin disease which comprises administering to said mammal an anti-hyperproliferative effective amount of a pharmaceutical composition containing as an active ingredient a compound having the structural formula I

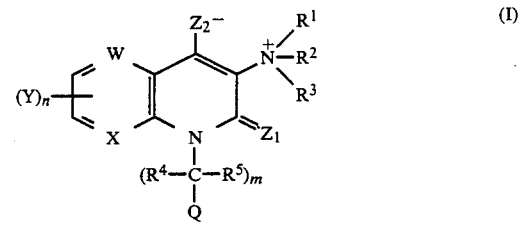

or a pharmaceutically acceptable salt or solvate thereof, wherein:

W and X may be the same or differnet and each independently represents —CH= or —N=;

$Z_1$ and $Z_2$ are the same or different and each independently represents O or S;

$R^1$, $R^2$, $R^3$, $R^4$ and $R^5$ are the same or different and each may be independently selected from the group consisting of H, alkyl having from 1 to 12 carbon atoms, alkenyl havign from 3 to 8 carbon atoms, alkynyl having from 3 to 8 carbon atoms, alkoxyalkyl having from 1 to 6 carbon atoms in the alkoxy portion and from 2 to 6 atoms in the alkyl portion thereof, hydroxyalkyl having from 2 to 8 carbon atoms, cycloalkyl having from 3 to 8 carbon atoms, acyloxyalkyl having from 1 to 6 carbon atoms in the acyloxy portion and from 2 to 8 carbon atoms in the alkyl portion thereof, and —$R^6$—$CO_2R^0$ wherein $R^6$ represents an alyklene group having from 1 to 6 carbon atoms and $R^0$ represents hydrogen or an alkyl group having from 1 to 6 carbon atoms, with the provisos that the OH of the hydroxyalkyl grop and the acyloxy of the acyloxyalkyl group are not joined to the same carbon atom as another heteroatom and that when $R^1$, $R^2$, and/or $R^3$ are alkenyl or alkynyl, there is at least one carbon-carbon single bond between the nitrogen atom and the carbon-carbon double or triple bond;

in addition, one of $R^1$, $R^2$ or $R^3$ can be an aryl group containing 6 to 15 carbon atoms or an aromatic heterocyclic group containing 3 to 14 carbon atoms, either of which can be substituted with one to three substituents Y as defined below;

in further addition, two of $R^1$, $R^2$ and $R^3$ can be joined together to represent an imidazolyl ring or to represent a ring which can contain from 2 to 8 carbon atoms, said ring optionally containing a —O—, —S— and/or —NR$^4$— heteroatomic group (wherein $R^4$ is as defined above) and/or optionally containing a carbon-carbon double bond, and said ring optionally being substituted with one to three additional substitutents $R^7$ which substituents may be the same or different and are each independently selected from OH with the proviso that OH is not on a carbon already joined to a hetero atom, —O-acyl having from 1 to 6 carbon atoms, hdroxyalkyl having from 1 to 8 carbon atoms, alkoxyalkyl having from 1 to 6 carbon atoms in each alkyl portion thereof, alkyl having from to 1 to 6 carbon atoms, alkenyl having from 3 to 8 carobn atoms, alkynyl having from 3 to 8 carbon atoms, —COOR$^{10}$ wherein $R^{10}$ is H, akyl or aryl containing from 6–15 carbon atoms, or any two $R^7$ substituent groups may represent a hydrocarbon ring having from 4 to 8 total carbon atoms;

in still further addition, all three of $R^1$, $R^2$ and $R^3$ can be joined together to represent a polycyclic ring, which polycyclic ring can optionally be substituted by one to three substituents groups $R^7$ defined above;

m is an integer of from 0 to 3;

n is an integer of from 0 to 2;

Q represents an aryl containing 6 to 15 carbon atoms or an aromatic heterocyclic group containing 3 to 14 carbon atoms, either of which group can optionally be substituted with 1 to 3 substitutents Y as defined below;

each Y substituent is independently selected from the group consisting of hydroxy, alkyl having from 1 to 6 carbon atoms, halogen, $NO_2$, alkxoy having from 1 to 6 carbon atoms, trifluoromethyl, cyano, cycloalkyl having from 3 to 7 carbon atoms, alkenyloxy having from 3 to 6 carbon atoms, alkynyloxy having 3 to 6 carbon atoms, hydroxyalkyl having from 1 to 6 carbon atoms, —S(O)$_n$—R$^8$ (wherein $R^8$ represents alkyl having from 1 to 6 carbon atoms and n is as defined above), —SO$_2$NH$_2$, —CO—R$^9$ (wherein $R^9$ represents OH, —NH—R$^8$ or —O—R$^8$, where $R^8$ is as defined above), —O—B—COR$^9$ (wherein B represents an alkylene group having from 1 to 4 carbon atoms and $R^9$ is as defined above), —NH$_2$, —NHCHO, —NH—CO—R$^9$ (wherein $R^9$ is as defined above, with the proviso that it is into hydroxy), —NH—COCF$_3$, —NH—SO$_2$R$^8$ (wherein $R^8$ is as defined above), and —NHSO$_2$CF$_3$.

17. A method according to claim 13, wherein in the compound of formula I at least one of W and X is —N═.

18. A method according to claim 13, wherein in the compound of formula I X is —N═ and W is —CH═.

19. A method according to claim 14, wherein in the compound of formula I and least one of W and X is —N═.

20. A method according to claim 14, wherein in the compound of formula I X is —N═ and W is —CH═.

21. A method according to claim 15, wherein in the compound of formula I at least one of W and X is —N═.

22. A method according to claim 15, wherein in the compound of formula I, X is —N═ and W is —CH═.

23. A method according to claim 16, wherein in the compound of formula I at least one of X and W is —N═.

24. A method according to claim 16, wherein in the compound of formula I X is —N═ and W is —CH═.

25. A method according to claim 13, wherein the active ingredient is a compound of formula II

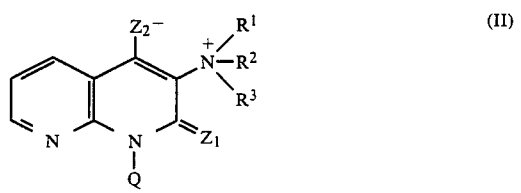

(II)

or a pharmaceutically acceptable salt or solvate thereof, wherein $R^1$, $R^2$, $R^3$, Q, $Z_1$ and $Z_2$ are as defined in claim 13.

26. A method according to claim 25, wherein $Z_1$ and $Z_2$ are both O and Q represents a phenyl group, which may optionally be substituted with one or two Y groups.

27. A method according to claim 25, wherein the active ingredient is 1-(1,2-dihydro-4-hydroxy-1-phenyl-2-oxo-1,8-naphthyridin-3-yl-1-methylpyrrolidinium hydroxide, inner salt or a pharmaceutically acceptable salt or solvate thereof.

28. A method according to claim 25, wherein the active ingredient is 1-(1,2-dihydrol-4-hydroxy-1-phenyl-2-oxo-,18-naphthyridin-3-yl)pyrrolidinium hydroxide, inner salt or a pharmaceutically acceptable salt or solvate thereof.

29. A method according to claim 14, wherein the active ingredient is a compound of formula II

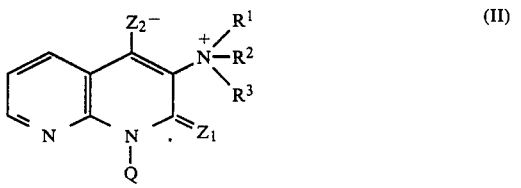

(II)

or a pharmaceutically acceptable salt or solvate thereof, wherein $R^1$, $R^2$, $R^3$, Q, $Z_1$ and $Z_2$ are as defined in claim 14.

30. A method according to claim 29, wherein $Z_1$ and $Z_2$ are both O and Q represents a phenyl group, which may optionally be substituted with one or two Y groups.

31. A method according to claim 29, wherein the active ingredient is 1-(1,2-dihydro-4-hydroxy-1-phenyl-2-oxo-1,8-naphthyridin-3-yl-1-methylpyrrolidinium hydroxide, inner salt or a pharmaceutically acceptable salt or solvate thereof.

32. A method according to claim 29, wherein the active ingredient is 1-(1,2-dihydro-4-hydroxy-1-phenyl-2-oxo-1,8-naphthyridin-3-yl)pyrrolidinium hydroxide, inner salt or a pharmaceutically acceptable salt or solvate thereof.

33. A method according to claim 15, wherein the active ingredient is a compound of formula II

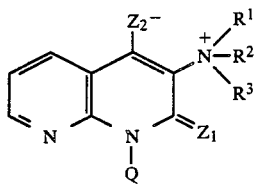

or a pharmaceutically acceptable salt or solvate thereof, wherein $R^1$, $R^2$, $R^3$, Q, $Z_1$ and $Z_2$ are as defined in claim 15.

34. A method according to claim 33, wherein $Z_1$ and $Z_2$ are both O and Q represents a phenyl group, which may optionally be substituted with one or two Y groups.

35. A method according to claim 33, wherein the active ingredient is 1-(1,2-dihydro-4-hydroxy-1-phenyl-2-oxo-1,8-naphthyridin-3-yl-1-methylpyrrolidinium hydroxide, inner salt or a pharmaceutically acceptable salt or solvate thereof.

36. A method according to claim 33, wherein the active ingredient is 1-(1,2-dihydro-4-hydroxy-1-phenyl-2-oxo-1,8-naphthyridin-3-yl)pyrrolidinium hydroxide, inner salt or a pharmaceutically acceptable salt or solvate thereof.

37. A method according to claim 16, wherein the active ingredient is a compound of formula II

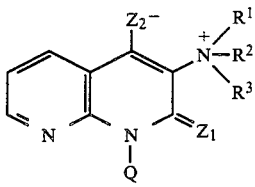

or a pharmaceutically acceptable salt or solvate thereof, wherein $R^1$, $R^2$, $R^3$, Q, $Z_1$ and $Z_2$ are as defined in claim 16.

38. A method according to claim 37, wherein $Z_1$ and $Z_2$ are both O and Q represents a phenyl group, which may optionally be substituted with one or two Y groups.

39. A method according to claim 37, wherein the active ingredient is 1-(1,2-dihdyro-4-hydroxy-1-phenyl-2-oxo-1,8-naphthyridin-3-yl-1-methylpyrrolidinium hydroxide, inner salt or a pharmaceutically acceptable salt or solvate thereof.

40. A method according to claim 37, wherein the active ingredient is 1-(1,2-dihydro-4-hydroxyl-1-phenyl-2-oxo-1,8-naphthyridin-3-yl)pyrrolidinium hydroxide, inner salt or a pharmaceutically acceptable salt or solvate thereof.

* * * * *